United States Patent
Watanabe et al.

(10) Patent No.: US 9,918,756 B2
(45) Date of Patent: Mar. 20, 2018

(54) REDUCING IMPLANT STRESS ZONES

(75) Inventors: Kohsuke Watanabe, Memphis, TN (US); Henry B. Faber, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 89 days.

(21) Appl. No.: 14/232,953

(22) PCT Filed: Jul. 13, 2012

(86) PCT No.: PCT/US2012/046681
§ 371 (c)(1),
(2), (4) Date: Jan. 16, 2014

(87) PCT Pub. No.: WO2013/012727
PCT Pub. Date: Jan. 24, 2013

(65) Prior Publication Data
US 2014/0316409 A1    Oct. 23, 2014

Related U.S. Application Data

(60) Provisional application No. 61/508,429, filed on Jul. 15, 2011.

(51) Int. Cl.
*A61B 17/58* (2006.01)
*A61B 17/72* (2006.01)
*A61L 31/12* (2006.01)

(52) U.S. Cl.
CPC ............ *A61B 17/72* (2013.01); *A61L 31/126* (2013.01)

(58) Field of Classification Search
CPC . A61B 17/72; A61B 17/7233; A61B 17/1725; A61B 17/7241
USPC .................................................... 606/62–68
See application file for complete search history.

(56) References Cited

U.S. PATENT DOCUMENTS

| | | | |
|---|---|---|---|
| 4,628,920 A | | 12/1986 | Mathys et al. |
| 4,784,127 A | | 11/1988 | Mattheck et al. |
| 5,129,904 A | * | 7/1992 | Illi .......... A61B 17/683 606/151 |
| 5,695,497 A | * | 12/1997 | Stahelin ........ F16B 23/0007 606/104 |

(Continued)

FOREIGN PATENT DOCUMENTS

| | | |
|---|---|---|
| CN | 101677831 A | 3/2010 |
| EP | 0311556 A2 | 4/1989 |

(Continued)

OTHER PUBLICATIONS

International Search Report; Korean Intellectual Property Office; International PCT Application No. PCT/US2012/046681; dated Jan. 22, 2013; 4 pages.

(Continued)

*Primary Examiner* — Eduardo C Robert
*Assistant Examiner* — Tara R Carter

(57) ABSTRACT

An orthopaedic implant includes a body being elongated in a longitudinal direction and having an outer wall, one or more openings through the outer wall, and a cannulation disposed along a length of the body and defined by the outer wall, the cannulation being non-uniform along the longitudinal direction, wherein the cannulation is configured such that a moment of inertia of the implant is substantially uniform along the longitudinal direction.

12 Claims, 3 Drawing Sheets

(56) References Cited

U.S. PATENT DOCUMENTS

| | | | |
|---|---|---|---|
| 6,106,528 A * | 8/2000 | Durham | A61B 17/1707 606/62 |
| 2001/0034523 A1 * | 10/2001 | Nelson | 606/62 |
| 2003/0139812 A1 * | 7/2003 | Garcia et al. | 623/17.11 |
| 2006/0161155 A1 * | 7/2006 | Schlienger et al. | 606/62 |
| 2006/0264948 A1 * | 11/2006 | Williams | 606/69 |
| 2007/0123878 A1 * | 5/2007 | Shaver | A61B 17/72 606/64 |
| 2007/0156144 A1 * | 7/2007 | Ulrich | A61B 17/7283 606/62 |
| 2008/0183292 A1 * | 7/2008 | Trieu | 623/17.11 |
| 2010/0174284 A1 | 7/2010 | Schwammberger et al. | |
| 2011/0087228 A1 * | 4/2011 | Ferrante et al. | 606/64 |
| 2011/0282395 A1 * | 11/2011 | Beyar et al. | 606/301 |

FOREIGN PATENT DOCUMENTS

| | | |
|---|---|---|
| WO | 89/07056 A1 | 8/1989 |
| WO | 1989/007056 A1 | 8/1989 |
| WO | 2008/147975 A1 | 12/2008 |
| WO | 2010/082183 A2 | 7/2010 |
| WO | 2011/044917 A1 | 4/2011 |

OTHER PUBLICATIONS

Written Opinion of the International Searching Authority; Korean Intellectual Property Office; International PCT Application No. PCT/US2012/046681; dated Jan. 22, 2013; 5 pages.

European Examination Report; European Patent Office; European Patent Application No. 12814523.2; dated Mar. 12, 2015; 9 pages.

Chinese Search Report; Chinese Patent Office; Chinese Patent Application No. 201280035183.X; dated Apr. 20, 2015; 6 pages.

Chinese First Office Action; Chinese Patent Office; Chinese Patent Application No. 201280035183.X; dated Apr. 28, 2015; 16 pages.

Chinese Second Office Action; Chinese Patent Office; Chinese Patent Application No. 201280035183.X; dated Feb. 15, 2016; 18 pages.

International Search Report; Korean Intellectual Property Office; International PCT Application No. PCT/US2012/046681; dated Jan. 22, 2013; 3 pages.

European Search Report; European Patent Office; European Patent Application No. 12814523.2; dated Mar. 12, 2015; 9 pages.

European Examination Report; European Patent Office; European Patent Application No. 12814523.2; dated Oct. 25, 2016; 6 pages.

Chinese Third Office Action; Chinese Patent Office; Chinese Patent Application No. 201280035183.X; dated Oct. 11, 2016; 8 pages.

* cited by examiner

REDUCING IMPLANT STRESS ZONES

CROSS-REFERENCE TO RELATED APPLICATION

This application is a U.S.National Phase filing of International Application No. PCT/US2012/046681 filed on Jul. 13, 2012 which claims priority to and the full benefit of U.S. Provisional Application Ser. No. 61/508,429, filed Jul. 15, 2011, and titled "Reducing Implant Stress Zones," the entire contents of which are incorporated herein by reference.

BACKGROUND

There are a variety of devices used to treat fractures of bones, such as the femur, humerus, and tibia. For example, fractures of the femur have been successfully treated with an orthopaedic implant, such as an intramedullary nail longitudinally placed within the medullary canal to connect the bone fragments.

SUMMARY

According to one aspect, an orthopaedic implant includes a body being elongated in a longitudinal direction and having an outer wall, one or more openings through the outer wall, and a cannulation disposed along a length of the body and defined by the outer wall, the cannulation being non-uniform along the longitudinal direction, wherein the cannulation is configured such that a moment of inertia of the implant is substantially uniform along the longitudinal direction.

Implementations of this aspect may include one or more of the following features. For example, a thickness of the outer wall may be substantially uniform along the longitudinal direction. A diameter of the cannulation at a proximal section of the body may be greater than a diameter of the cannulation at a distal section of the body. A thickness of the outer wall at the proximal section of the body may be substantially equal to a thickness of the outer wall at the distal section of the body. The cannulation may be disposed along an entire length of the body. The body may be made of carbon-fiber reinforced PEEK. The body may be made of metal.

According to another aspect, an orthopaedic implant includes a body being elongated in a longitudinal direction and having an outer wall, one or more openings through the outer wall, and a cannulation disposed along a length of the body and defined by the outer wall, the cannulation being substantially uniform along the longitudinal direction, wherein the body is configured such that stresses are evenly distributed along the longitudinal direction.

Implementations of this aspect may include one or more of the following features. For example, metal reinforcements may be placed in the body in areas of elevated stress. The body may include carbon-fiber reinforced PEEK layers, and the metal reinforcements may be placed between the carbon-fiber reinforced PEEK layers. Discrete sections along a length of the implant may be shaped to each have a moment of inertia that is optimized for evenly distributing stress. Discrete sections along a length of the implant may each have a material density that is optimized for evenly distributing stress. The implant may include carbon-fiber reinforced PEEK, and the material density may be optimized by varying a percentage of carbon-fiber reinforcement The implant further may further include PAEK. The implant may further include one or more pockets or cavities configured to weaken the implant in particular sections to more evenly distribute stress. The cannulation may be disposed along an entire length of the body. The body may be made of carbon-fiber reinforced PEEK. The body may be made of metal.

DETAILED DESCRIPTION

Figure 1:
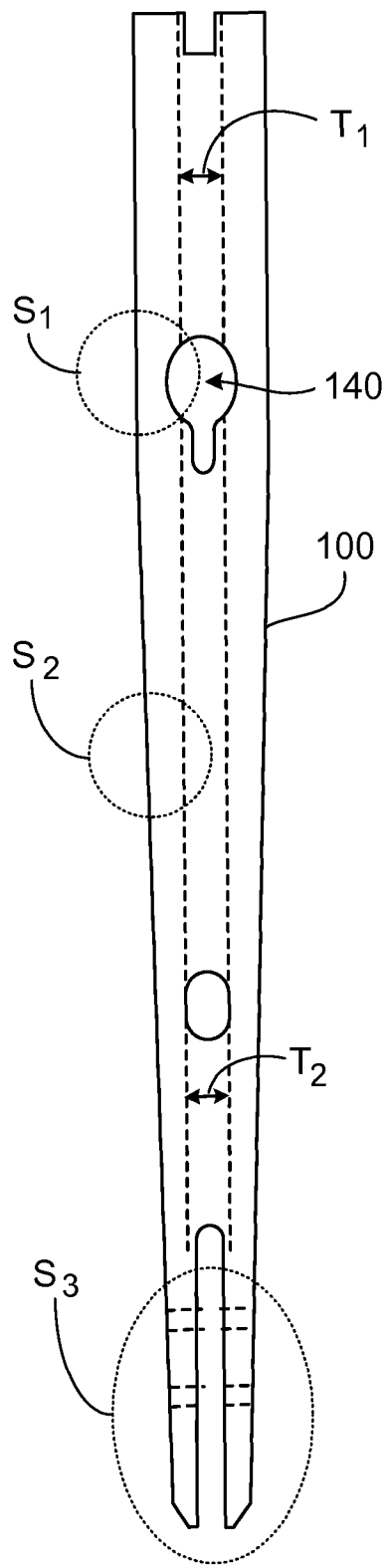
FIG. 1 is a perspective view of an orthopaedic implant with a uniform cannulation

FIG. 1 illustrates an intramedullary nail 100 of the prior art having stress zones S1, S2, and S3. The stress zones S1, S2, and S3 may be identified through the use of finite element analysis. The stress zones S1, S2, and S3 typically occur where there is a change in material thickness and/or shape and/or moment of inertia. In the depicted embodiment, S1 is located near proximal locking holes, S2 occurs at a point where the nail 100 changes shape and diameter, and S3 occurs near the distal locking holes. The intramedullary nail 100 has a cannulation 140 with a uniform size or diameter. In other words, a measurement of the width T1 in the proximal section of the cannulation is equal to a measurement of the width T2 in the distal section of the cannulation 140. T1 and T2 illustrate that the size or diameter of the cannulation 140 is substantially uniform. In the prior art, the cannulation 140 has a substantially uniform size to keep manufacturing costs low. However, having the cannulation 140 of uniform size causes the wall thickness and moment of inertia of the nail 100 to vary, which leads to stress risers in certain locations. In addition, having the cannulation 140 of substantially uniform size causes the moment of inertia of the nail 100 to vary along a longitudinal portion of the nail 100, which can also have detrimental effects.

Figure 2:
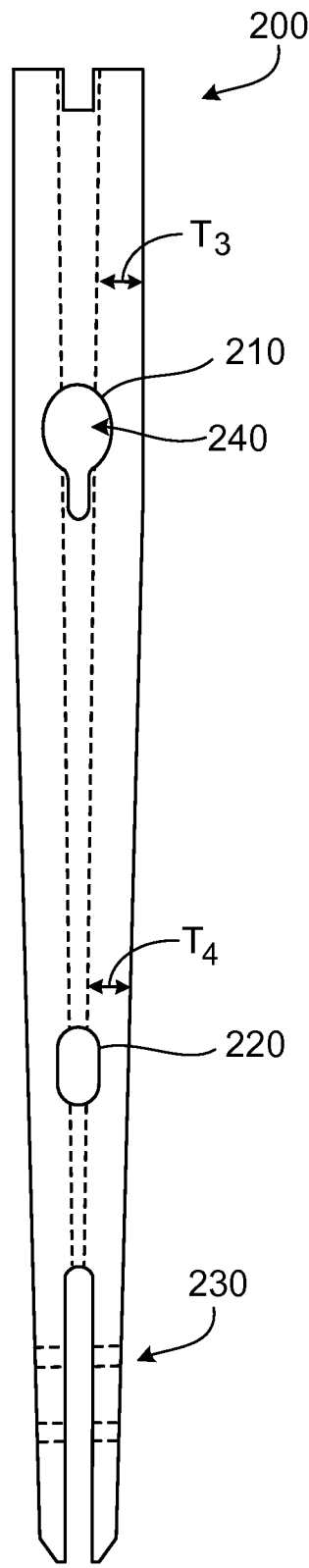
FIG. 2 is a perspective view of an orthopaedic implant with a non-uniform cannulation

In one implementation, an orthopaedic implant has a substantially uniform moment of inertia. As an example, FIG. 2 illustrates an intramedullary nail 200. The intramedullary 200 has a proximal locking hole 210, distal locking holes 230, and a cannulation 240. In some cases, the intramedullary nail 200 has a dynamizing slot 220. The intramedullary 200 may be made of carbon-fiber reinforced PEEK or metal, such as titanium or stainless steel. The cannulation 240 is non-uniform in a longitudinal direction such that even with a change in diameter and/or shape the moment of inertia of the intramedullary nail 200 is maintained generally uniform. As shown in FIG. 2, even with a change in diameter and/or shape, the moment of inertia can be substantially uniform along the longitudinal portion of the nail 200 as a result of maintaining the uniformity of the wall thickness of the nail 200 along the longitudinal portion of the nail 200. Additionally, the wall thickness of the proximal section T3 can be substantially the same as the wall thickness T4 of the distal section. Having a generally uniform moment of inertia can reduce stress risers and allow for a more even distribution of stress. Moreover, having a generally uniform wall thickness can help limit fluctuations in the moment of inertia along the longitudinal portion of the device, which can improve performance characteristics of the device.

In an alternative implementation, the cannulation 240 can be uniform, and metal reinforcements may be placed in areas of elevated stress. The metal reinforcements can be placed in precise locations based upon, for example, finite element analysis to more evenly distribute stress. In some cases, the metal reinforcements may be placed between carbon-fiber reinforced PEEK layers.

In another alternative implementation, the cannulation 240 can be uniform, but discrete sections of the intramedullary nail may be modified in shape to more evenly distribute stress. For example, by using finite element analysis data and the moment of inertia of each discrete section, the nail can be designed to evenly distribute stress.

In yet another alternative implementation, the cannulation 240 can be uniform, but discrete sections of the intramedullary nail may be modified in material to more evenly distribute stress. For example, by using finite element analysis data and the density of the material in each discrete section, the nail can be designed to evenly distribute stress. In some cases, selected sections of a carbon-fiber reinforced PEEK nail may have more or less percentage of carbon-fiber reinforcement. Alternatively, or additionally, a different type of polymer, such as PAEK, may be used instead of PEEK in some sections.

In still another alternative implementation, the cannulation 240 can be uniform, but discrete sections of the intramedullary nail may be designed to include a pocket or a cavity to weaken the nail in particular sections to more evenly distribute stress.

Figure 3:
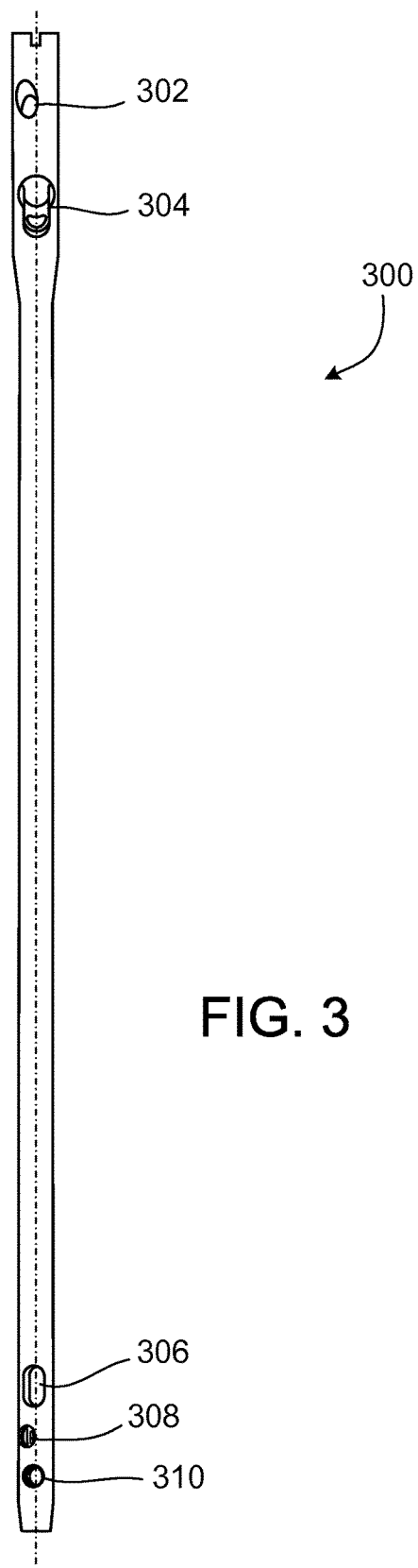
FIG. 3 is a perspective view n intramedullary nail.

The techniques described above for reducing stress zones can he applied to other configurations of intramedullary nails for the long or short bones, such as an intramedullary nail 300 illustrated in FIG. 3, Preferably, regions around locking holes 302, 304, 306, 308, and 310 may be modified as described above to more evenly distribute stress.

What is claimed is:

1. An orthopaedic implant comprising:
   a body being elongated in a longitudinal direction and having an outer wall;
   one or more openings through the outer wall; and
   a cannulation disposed along a length of the body and defined by the outer wall, the cannulation being substantially uniform along the longitudinal direction, and
   wherein a thickness of the outer wall positioned about the cannulation is substantially uniform along the longitudinal portion of the body,
   wherein the body is configured such that stresses are evenly distributed along the longitudinal direction,
   wherein discrete sections along a length of the implant each have a material density that is different than a material density of other portions of the implant and which is optimized for evenly distributing stress.

2. The orthopaedic implant of claim 1, wherein the cannulation extends from a proximal end to a distal end of the body.

3. The orthopaedic implant of claim 1, wherein the body comprises a polymer material.

4. The orthopaedic implant of claim 3, wherein the body comprises carbon-fiber reinforced PEEK layers.

5. The orthopaedic implant of claim 1, wherein the implant comprises carbon-fiber reinforced PEEK, and wherein the material density is optimized by varying a percentage of carbon-fiber reinforcement at the discrete sections of the implant in areas of elevated stress.

6. The orthopaedic implant of claim 5, wherein the implant further comprises PAEK material at the discrete sections of the implant in the areas of elevated stress.

7. The orthopaedic implant of claim 1, further comprising one or more pockets or cavities configured to weaken the implant in particular sections to more evenly distribute stress in the implant along the longitudinal direction.

8. The orthopaedic implant of claim 1, wherein the cannulation is disposed along an entire length of the body.

9. The orthopaedic implant of claim 1, wherein the body is made of carbon-fiber reinforced PEEK.

10. The orthopaedic implant of claim 1, wherein the body is made of metal.

11. The orthopaedic implant of claim 1, wherein the discrete sections of the body comprise regions around the one or more openings through the outer wall of the body.

12. The orthopaedic implant of claim 1, wherein the body comprises a polymer material.

* * * * *